US00PP20471P2

(12) United States Plant Patent
Zlesak

(10) Patent No.: US PP20,471 P2
(45) Date of Patent: Nov. 10, 2009

(54) SHRUB ROSE PLANT NAMED 'ZLEMARTINCIPAR'

(50) Latin Name: *Rosa hybrida*
Varietal Denomination: ZLEMartinCipar

(76) Inventor: David Charles Zlesak, 1500 Fairmount Ave., St. Paul, MN (US) 55105

( * ) Notice: Subject to any disclaimer, the term of this patent is extended or adjusted under 35 U.S.C. 154(b) by 0 days.

(21) Appl. No.: 12/221,397

(22) Filed: Aug. 4, 2008

(51) Int. Cl.
*A01H 5/00* (2006.01)

(52) U.S. Cl. ..... Plt./108
(58) Field of Classification Search ..... Plt./108, Plt./102
See application file for complete search history.

*Primary Examiner*—Annette H Para

(57) ABSTRACT

Shrub rose plant having an upright, spreading plant habit; large clusters of flowers borne in panicles; flowers have five petals each; petals are a rich red color; continuous flowering throughout the growing season; resistance to major fungal diseases and ability to root and grow vigorously from softwood and semi-hardwood cuttings.

6 Drawing Sheets

Latin name of the plant claimed: *Rosa hybrida.*
Variety denomination: 'ZLEMartinCipar'.

BACKGROUND OF THE INVENTION

The primary objective of making this cross was to produce a new rose variety having the continuous blooming habit, dark magenta petal margins, and winter hardiness of the female parent and the vigor, disease resistance, and abundance of flowers of the male parent. The pollination occurred in late spring 2000. The seed germinated during the winter of 2000/2001 and 'ZLEMartinCipar' was identified and first asexually propagated in 2001.

The present invention relates to a new and distinct variety of rose plant of the shrub commercial class designated 'ZLEMartinCipar' which was originated by me by crossing an unnamed seedling (1997-1) of the polyantha commercial rose class with 'Robin Hood', a cultivar of the hybrid musk commercial rose class (not patented).

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Upright, spreading plant habit;
2. Large clusters of flowers borne in panicles;
3. Flowers that primarily have five petals each;
4. A rich red petal color;
5. Continuous flowering throughout the growing season;
6. Resistance to major fungal diseases;
7. Ability to root and grow vigorously from softwood and semi-hardwood cuttings.

Asexual reproduction of this new variety by rooting softwood and semi-hardwood cuttings, as performed at St. Paul, Minn., shows that the foregoing and all other characteristics and distinctions come true to form and are established and transmitted through succeeding propagations.

Comparison with Parents

'ZLEMartinCipar' has single red flowers and an upright spreading plant habit which differs from the female parent, 1997-1, which has single blooms with primarily white petals and a dark magenta petal margin and a compact rounded plant habit.

'ZLEMartinCipar' differs from the male parent, 'Robin Hood', in that 'Robin Hood' has flowers with typically more than 10 petals, light-red to dark pink petals with white petal bases and is less winter hardy. In a single garden bed in St. Paul, Minn. (United States Department of Agriculture cold hardiness zone 4) from spring 2003 to spring 2007 there were four plants of 'Robin Hood' and six of 'ZLEMartinCipar' planted adjacently and cared for in a similar manner. By spring 2007 all the 'Robin Hood' roses died due to winter injury and all the plants of 'ZLEMartinCipar' were alive and grew into large, well-established plants.

Comparison with Similar Variety

The rose variety with the greatest similarity to 'ZLEMartinCipar' is 'Marjorie Fair' (not patented), a rose of the shrub commercial class. Both 'ZLEMartinCipar' and 'Marjorie Fair' have red, five-petaled blooms borne in panicles. Both roses also have an upright spreading plant habit. 'ZLEMartinCipar' has darker red flower color, a slightly more compact growth habit, and less prickles on the flowering lateral stems than 'Marjorie Fair'.

BRIEF DESCRIPTION OF THE DRAWINGS

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

Figure 1:
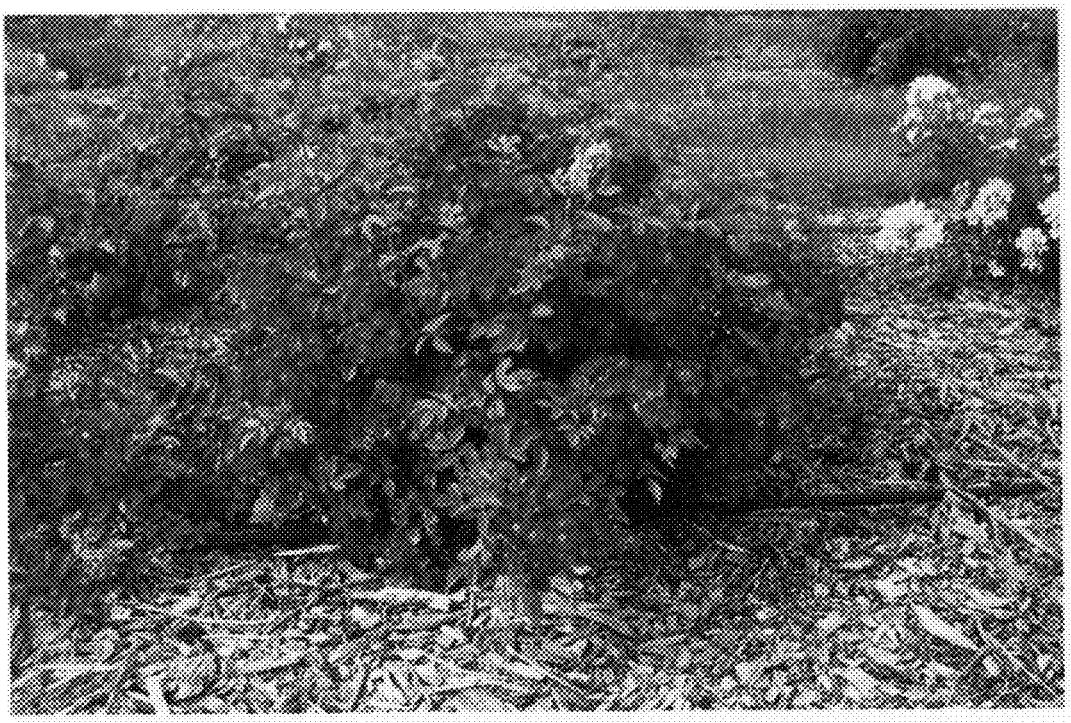
FIG. 1 illustrates a plant in its first cycle of bloom in June after being pruned to within 10 cm of the soil.
Figure 2:
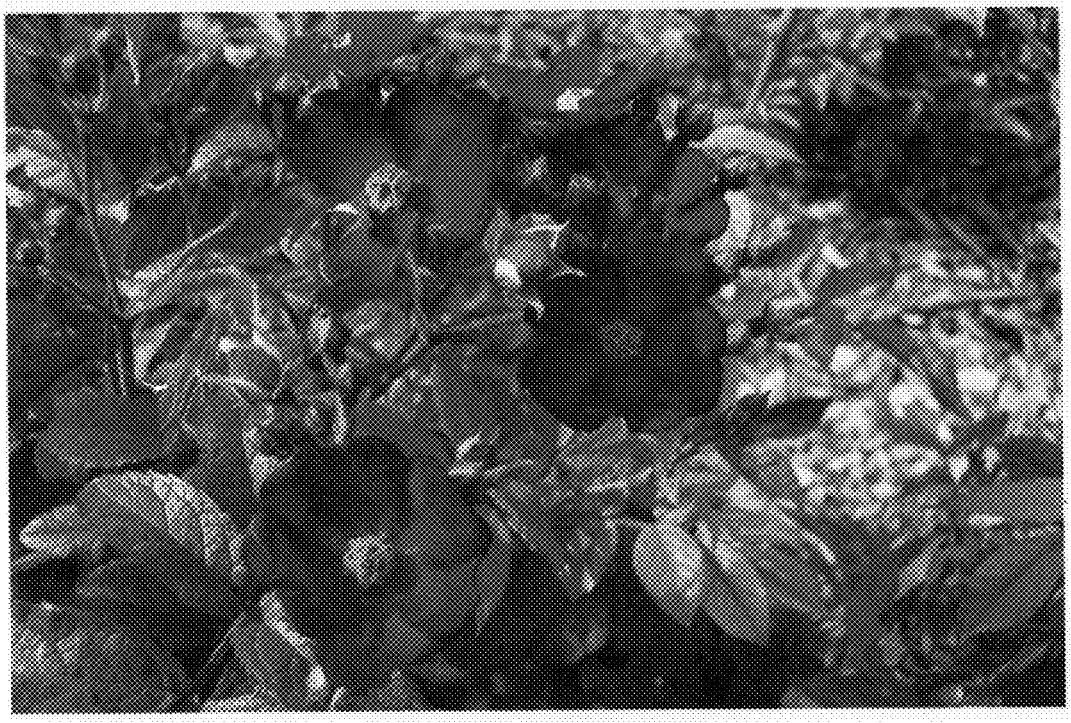
FIG. 2 illustrates a close up view of a group of flowers borne in a panicle.
Figure 3:
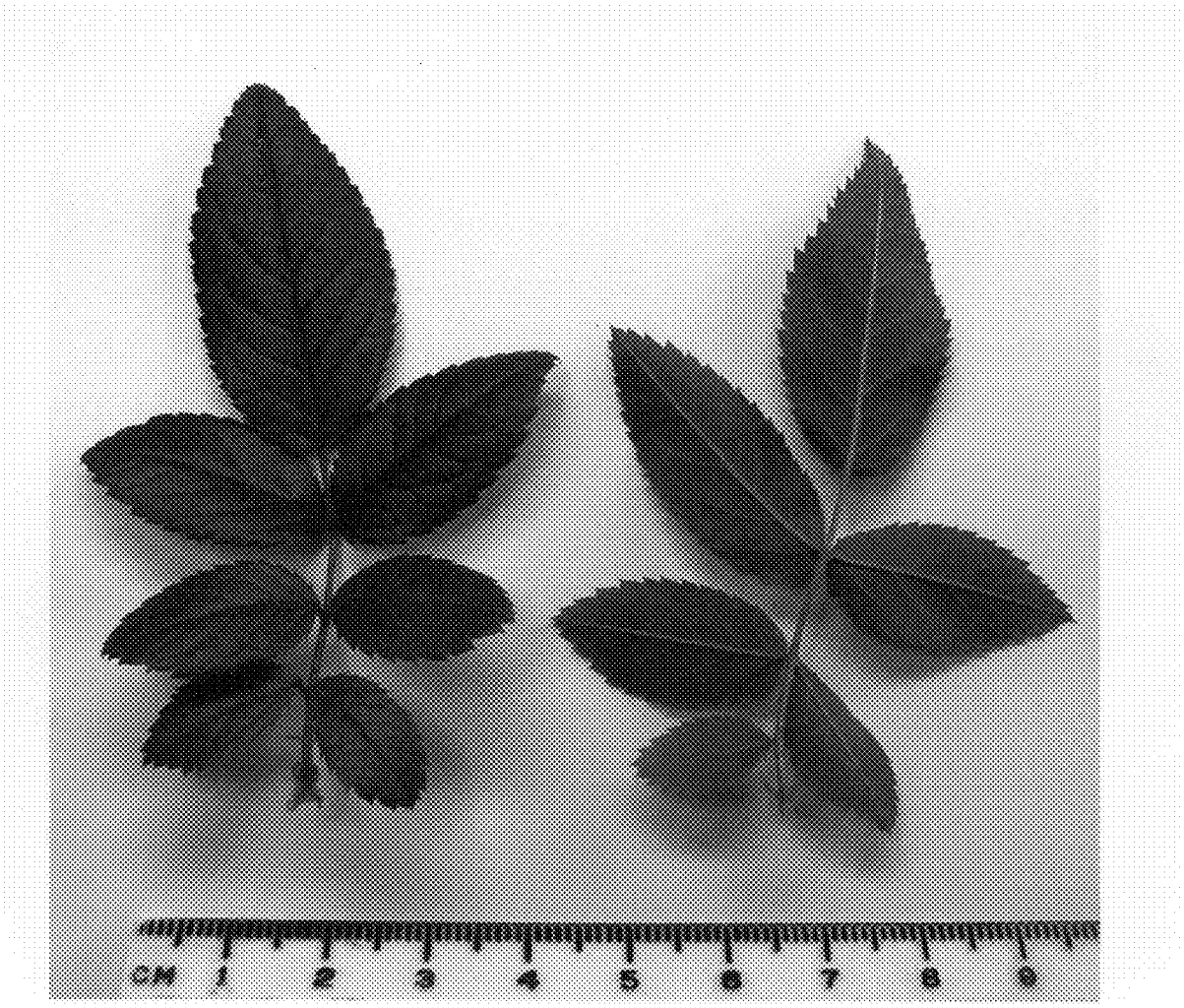
FIG. 3 illustrates representative fully expanded leaves and both the adaxial and abaxial surfaces.
Figure 4:
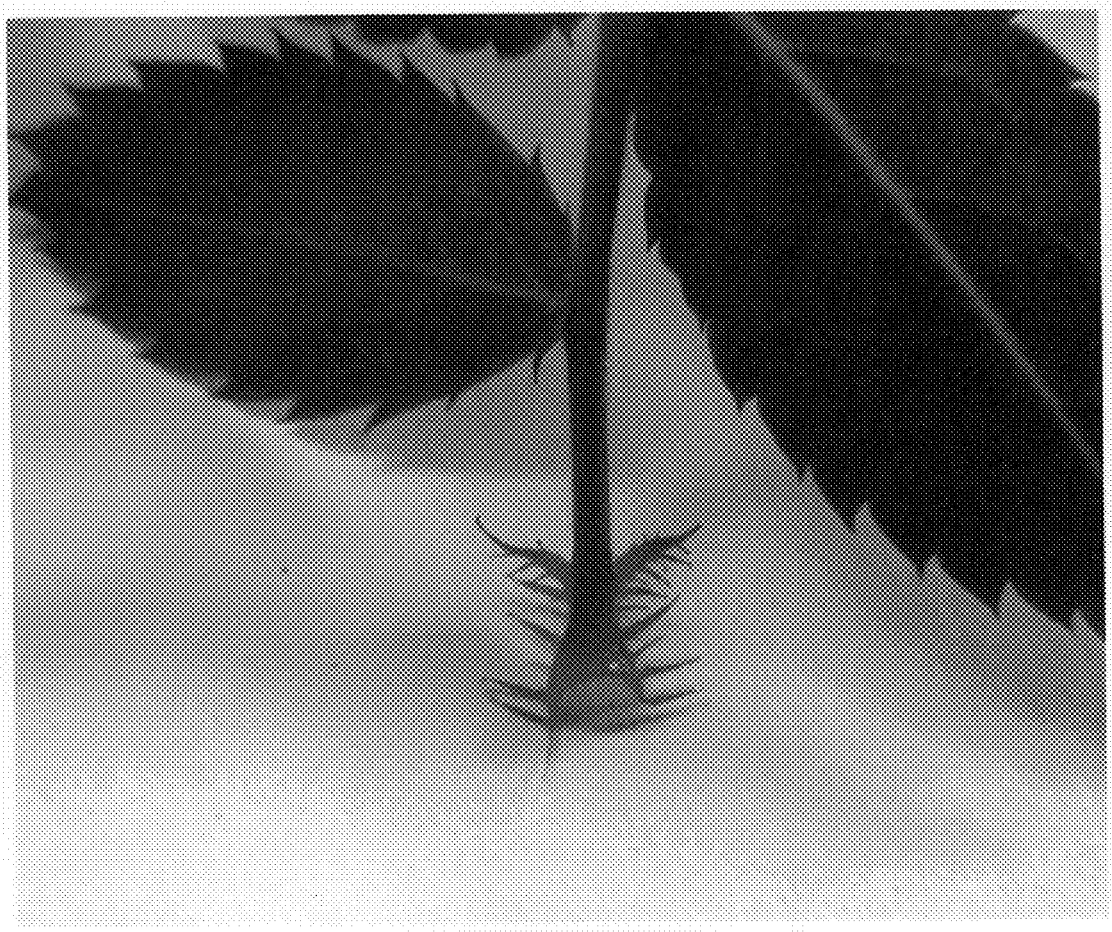
FIG. 4 illustrates the stipules from the abaxial side of a leaf base.
Figure 5:
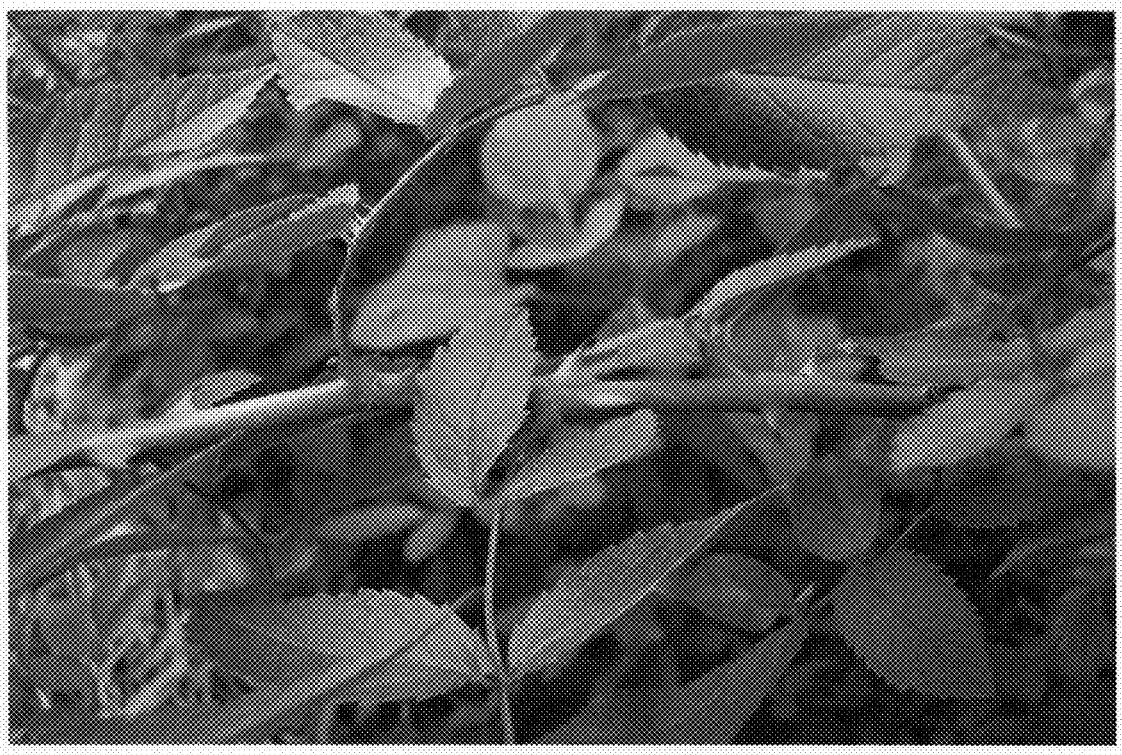
FIG. 5 illustrates prickles on a typical young, flowering stem.
Figure 6:
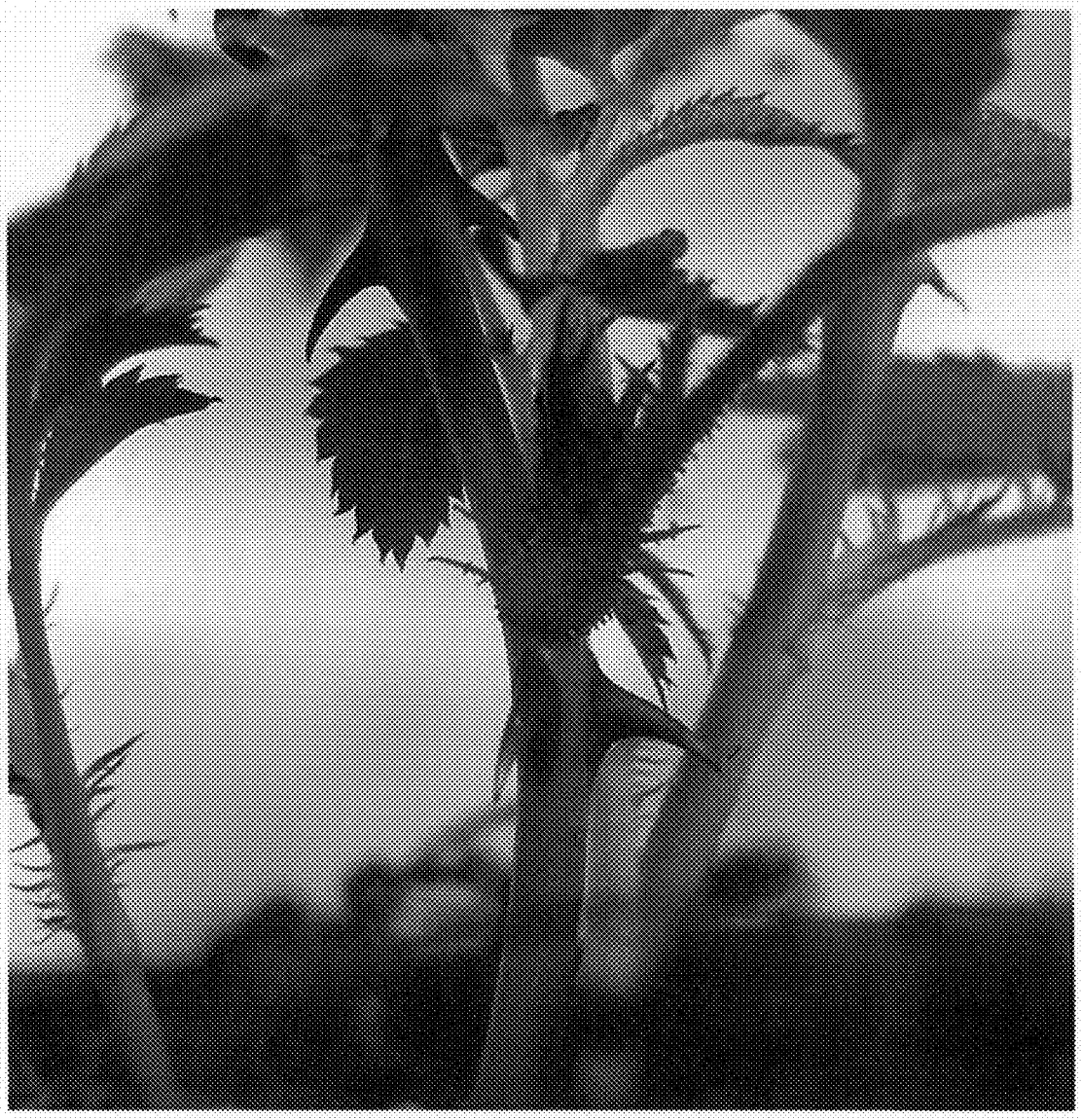
FIG. 6 illustrates prickles on an older stem with mature coloration.
Figure 7:
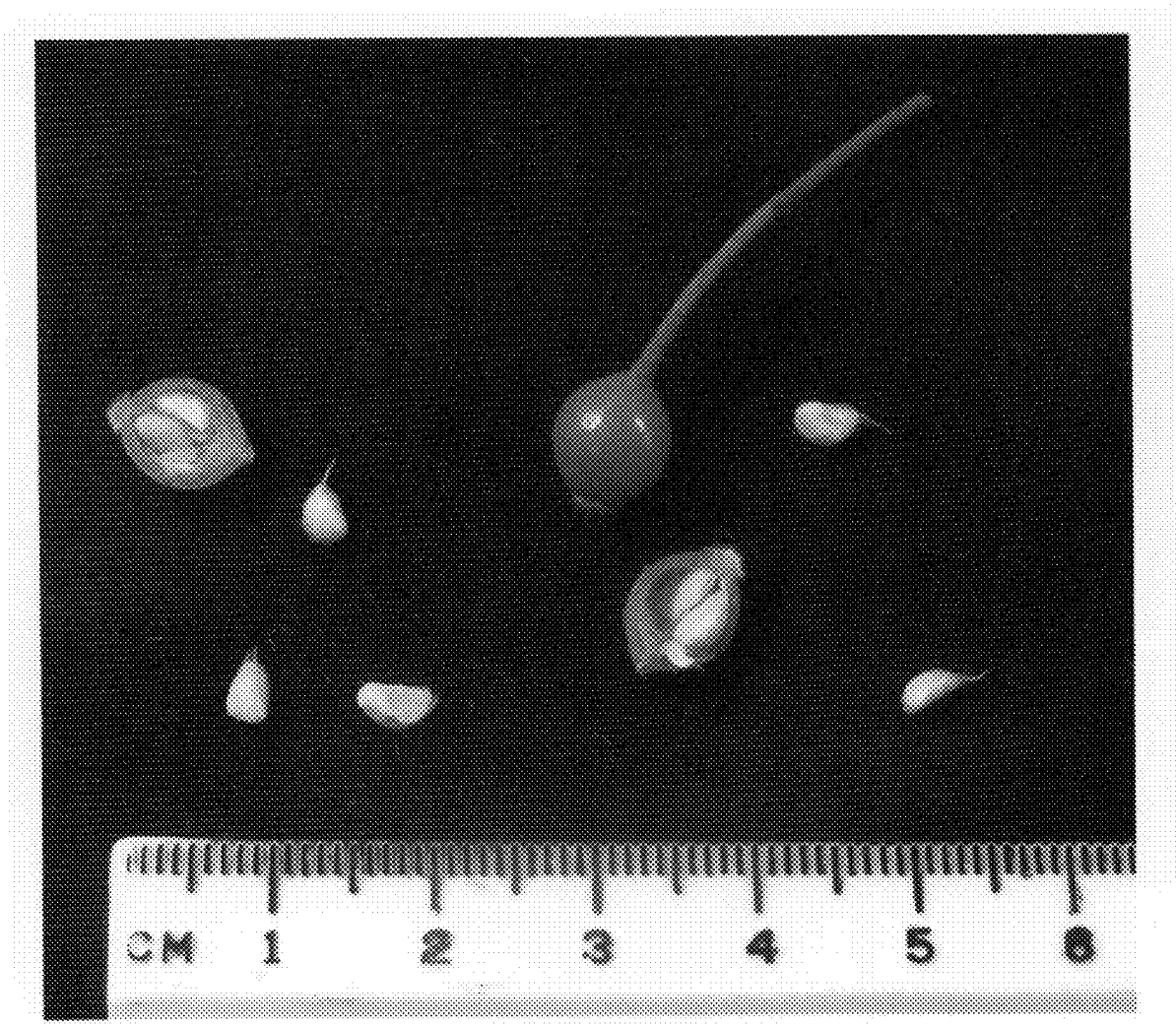
FIG. 7 illustrates a typical intact hip, cross section of a hip, and achenes.

The following is a detailed description of my new rose cultivar with color descriptions using terminology in accordance with The Royal Horticultural Society (London) Colour Chart (2001), except where ordinary dictionary significance of color is indicated. The phenotype of the new cultivar may vary with variations in environmental, climatic, and cultural conditions, as it has not been tested under all possible environmental conditions. Descriptions are based on observations of plants propagated from stem cuttings and are not grafted onto rootstock.

Parentage:

*Seed parent.*—An unnamed seedling never released for sale of the polyantha commercial rose class from my breeding program which I designate as 1997-1. It was selected from a population of seedlings derived from open pollinated seed collected and bulked from multiple unnamed rose seedlings of the polyantha commercial class that showed superior winter hardiness in Rhinelander, Wis. (United States Department of Agriculture cold hardiness zone 3).

*Pollen parent.*—'Robin Hood' (not patented). This rose is of the hybrid musk commercial rose class.

Classification:

*Botanical.*—*Rosa hybrida.*

*Commercial.*—Shrub.

Flower: Observations were made of plants six years of age propagated from cuttings and growing in tended gardens located in River Falls, Wis. and St. Paul, Minn.

Blooming habit: Continuous.

Bud:

*Size.*—6–10 mm long and 8–10 mm in diameter when the petals start to unfurl.

*Form.*—The bud form is pointed ovoid.

*Color.*—When sepals first divide, visible petal color is Red-Purple Group 59A. When half blown, the upper sides of the petals are closest to Red Group 53B and the lower sides of the petals are Red-Purple Group 58A.

*Sepals.*—Color: Yellow-Green Group 144B, often with Greyed-Purple Group 183C in areas exposed to bright sunlight and especially on the small glandular hairs exposed to bright sunlight. Length: 7–10 mm. Width: about 3 mm. Shape: ovate to oblong with acuminate tips. Surface texture: Adaxial, Hoary. Abaxial, Smooth with small glandular hairs. There are three lightly appendaged sepals. There are two unappendaged sepals and they have hoary edges.

*Receptacle.*—Color: Green Group 143C, sometimes with Greyed-Purple Group 183C. Shape: elliptic. Size: Small, about 3 mm wide and 4 mm long. Surface: Lightly covered in small white hairs.

*Peduncle.*—Length: Short, averaging about 10–16 mm. Surface: Lightly covered in glandular hairs. Color: Green Group 143C, often with areas of Greyed-Purple Group 183B. Strength: Stiff, primarily erect.

Bloom:

*Size.*—Small. Typical open diameter is 30–35 mm.

*Borne.*—A clusters of 12–30 blooms are borne in panicles on average sized stems. Larger stems arising from the base of the plant can produce panicles with 50–100 flowers.

*Stems.*—Strength: Strong. Length: Typically about 30–50 cm. Stem diameter: Varies and is typically 3–10 mm. Larger stems arising from the base of the plant are about 1 cm in diameter, while smaller stems arising from either the base of the plant or secondary or tertiary stems arising within the plant canopy are typically 3–6 mm in diameter.

*Form.*—When blooms first open: Slightly cupped to flat.

*Permanence.*—Blooms retain their form to the end.

*Petalage.*—Typically five.

*Color.*—The adaxial sides of the petals are primarily Red Group 53B and gradually transition to Red Group 53A toward the margin of the petal. The major color on the abaxial side of the petals is Red-Purple Group 58B. Sunlight is important for the development of the rich red flower color on especially the adaxial side of the petal. If petals overlap and direct sunlight is excluded from the adaxial side of a petal by an overlapping petal, the color of the covered petal surface is often pink and typically Red-Purple Group 57B.

*Discoloration.*—The general tonality of the adaxial petal surface of a fully open bloom at the first day through the third day: Red-Purple Group 53B. The general tonality of the adaxial petal surface at day ten: between Red-Purple Group 61C and Red Purple Group 63A. The abaxial surface of the petal usually remains a Red Purple Group 58A from opening to day ten.

*Fragrance.*—Slight. Character of fragrance: Spicy.

Petals:

*Texture.*—Thick and satiny to the touch.

*Length.*—1.5–1.7 cm.

*Width.*—1.5 cm.

*Shape.*—Obcordate.

*Margin.*—Entire.

*Apex shape.*—Obcordate and sometimes with a small point in the axis.

*Base shape.*—Cuneate.

*Form.*—Flat to slightly cupped.

*Arrangement.*—Single row of five evenly spaced, slightly overlapping petals.

*Petaloids.*—Typically none.

*Persistence.*—Petals drop off cleanly before drying.

*Lastingness.*—On the plant: Long (about 10 days). As a cut flower: Moderate (about 7 days).

Reproductive parts:

*Stamens.*—Number per flower: 50–80. Anthers — Size: Length before dehiscence: 1 mm, Width before dehiscence: 1 mm. Length after dehiscence: 0.5 mm. Width after dehiscence: 0.5 mm. Color: Yellow Orange Group 17A. Arrangement: Regular around styles. Filaments — Size: Length: 3–7 mm. Width: 0.25 mm. Color: Yellow Orange Group 17A. Pollen — Color: Yellow Orange Group 17C.

*Pistils.*—Number per flower: 8–15. Styles — Color: Yellow Green Group 145C. Length: 3–5 mm. Stigmas — Color: Yellow Green Group 145A. Ovary — Color of immature ovary: Yellow Green Group 145D.

*Hips.*—The fleshy portion of rose hips is hypanthium tissue and inside that tissue are achenes — individual fruits that develop into a single seeded fruit with a hard paricarp surrounding the embryo. Sepals naturally abscise from the hip and are not present upon ripening. Hypanthium: Color immature: Green Group 146B. Color mature: Greyed-Orange Group 169A. Shape: Rounded to slightly elliptical. Size: 9–11 mm long and 7–10 mm wide.

*Achenes* (*ripe*).—Color: Yellow Green Group 150D. Shape: Irregular. Size: 4–5 mm. Depending on pollination and fertilization success, there can be up to approximately 15 achenes (which are single seeded fruits) per hip. Typically there are 4–6 achenes per hip.

Plant:

*Form.*—Bush.

*Growth.*—Very vigorous, Upright, and branching.

*Age at maturity.*—3 years.

*Mature plant.*—Height is 100 cm and width is 130 cm.

*Foliage.*—Number of leaflets on typical leaves: seven.

*Size.*—Medium (12 cm long and 7.5 cm wide).

*Quantity.*—Normal.

*Color.*—New foliage: Adaxial side: Yellow-Green Group 146A Abaxial side: Yellow Green Group 146B, but frequently when growing in high light the color is Greyed-Red Group 178B. Old foliage: Adaxial side: Green Group 139A. Abaxial side: Green Group 137C.

Leaflets:

*Size.*—Terminal leaflets: Medium (5–6 cm long and 2.0–2.3 cm wide). Non-terminal leaflets: Medium (3–4 cm long and 1.5–2.0 cm wide).

*Shape.*—Ovate.

*Base shape.*—Obtuse.

*Apex shape.*—Acute.

*Texture.*—Semi-glossy, rugose.

*Edge.*—Serrated.

*Serrations.*—Single, small.

*Petiole.*—Color — Green Group 137B.

*Petiole rachis.*—Color: Yellow-Green Group 146B and sometimes with Greyed-Purple Group 183D highlights on especially the adaxial side especially in high light.

*Petiole underside.*—Rough with glandular hairs and small prickles. Prickles can have highlights of Greyed-Purple Group 183C especially if grown in high light.

*Stipules.*—Short (about 1.0–1.2 cm in length). Color: Green Group 137C, edges with several relatively parallel and narrow appendages (1–3 mm long and 0.25 mm wide).

*Disease resistance.*—Resistant to mildew, blackspot, and rust under normal growing conditions.

*Pest persistence.*—Not observed.

*Veination pattern.*—Pinnate reticulate.

*Veination color.*—The color of the veins is the same or very close to that of the overall leaf blade. New foliage: Adaxial side: Yellow-Green Group 146A Abaxial side: Yellow Green Group 146B. Old foliage: Adaxial side: Green Group 139A. Abaxial side: Green Group 137C.

Wood:

*New wood.*—Color: Yellow-Green Group 144B. Bark: Smooth.

*Old wood.*—Color: Green Group 143A. Bark: Smooth.

Typical stem prickles:

*Quantity.*—Ten to 15 typically on a 15 cm length of stem.

*Form.*—Hooked slightly downward.

*Length.*—5–7 mm.

*Color when young.*—Green Group 142B with areas suffused with Greyed-Red Group 180B especially if exposed to bright sunlight.

*Color when mature.*—Greyed-Purple Group N186C.

Small stem prickles:

*Quantity.*—On main stems: None. On laterals close to flowers: Present in relatively low quantities.

*Form.*—Hooked slightly downward or straight.

*Length.*—Typically less than 3 mm.

*Color when young.*—Green Group 142B with areas suffused with Greyed-Red Group 180B.

*Color when mature.*—Greyed-Purple Group N186C.

Cytology:

*Ploidy.*—Diploid (2n=2x=14). Meristematic root tip cells in the stage of metaphase of mitosis were observed to have 14 chromosomes under a light microscope at 400× magnification.

Winter hardiness: Consistently crown hardy to United States Department of Agriculture cold hardiness zone 4.

I claim:

1. A new and distinct variety of rose plant of the shrub class, substantially as herein shown and described, characterized particularly by its upright, spreading plant habit; large clusters of flowers borne in panicles; flowers that primarily have five petals each; petals are a rich red color; continuous flowering throughout the growing season; resistance to major fungal diseases and ability to root and grow vigorously from softwood and semi-hardwood cuttings.

* * * * *